US008891895B2

(12) United States Patent
Garrett et al.

(10) Patent No.: US 8,891,895 B2
(45) Date of Patent: Nov. 18, 2014

(54) SYSTEMS AND METHODS FOR IMAGING OF FALLING OBJECTS

(75) Inventors: Tim Garrett, Salt Lake City, UT (US); Cale Fallgatter, Salt Lake City, UT (US)

(73) Assignee: University of Utah Research Foundation, Salt Lake City, UT (US)

( * ) Notice: Subject to any disclaimer, the term of this patent is extended or adjusted under 35 U.S.C. 154(b) by 264 days.

(21) Appl. No.: 13/514,716

(22) PCT Filed: Dec. 9, 2010

(86) PCT No.: PCT/US2010/059755
§ 371 (c)(1),
(2), (4) Date: Nov. 8, 2012

(87) PCT Pub. No.: WO2011/072157
PCT Pub. Date: Jun. 16, 2011

(65) Prior Publication Data
US 2013/0051696 A1    Feb. 28, 2013

Related U.S. Application Data

(60) Provisional application No. 61/267,952, filed on Dec. 9, 2009.

(51) Int. Cl.
| G06K 9/40 | (2006.01) |
| G01N 21/01 | (2006.01) |
| G01B 11/245 | (2006.01) |
| G01W 1/14 | (2006.01) |
| G01N 21/85 | (2006.01) |

(52) U.S. Cl.
CPC ............... *G01B 11/245* (2013.01); *G01N 21/01* (2013.01); *G01N 2021/8592* (2013.01); *G01N 21/85* (2013.01); *G01W 1/14* (2013.01)
USPC ............ 382/254; 382/100; 382/260; 382/274

(58) Field of Classification Search
CPC ............. G02B 27/0178; G02B 27/017; G02B 27/0093; G06F 3/013; G02C 7/08
USPC ............... 382/100, 254, 260, 274; 250/208.1, 250/573; 345/633, 8, 156
See application file for complete search history.

(56) References Cited

U.S. PATENT DOCUMENTS

| 4,561,018 A | 12/1985 | Berthel et al. |
| 2007/0132599 A1 | 6/2007 | DuFaux et al. |

(Continued)

FOREIGN PATENT DOCUMENTS

| JP | 08-201534 | 8/1996 |
| JP | 2000-275357 | 10/2000 |
| JP | 2001-021669 | 1/2001 |
| KR | 2008-0046339 | 5/2008 |

OTHER PUBLICATIONS

PCT/US2010/059755; filed Dec. 9, 2010; Fallgatter et al.; international search report dated Sep. 23, 2011.

(Continued)

*Primary Examiner* — Ali Bayat
(74) *Attorney, Agent, or Firm* — Thorpe North & Western LLP (57) ABSTRACT

Imaging of falling objects is described. Multiple images of a falling object can be captured substantially simultaneously using multiple cameras located at multiple angles around the falling object. An epipolar geometry of the captured images can be determined. The images can be rectified to parallelize epipolar lines of the epipolar geometry. Correspondence points between the images can be identified. At least a portion of the falling object can be digitally reconstructed using the identified correspondence points to create a digital reconstruction.

20 Claims, 7 Drawing Sheets

(56) References Cited

U.S. PATENT DOCUMENTS

2009/0016636 A1* 1/2009 Kasashima et al. ............ 382/274
2009/0040297 A1* 2/2009 Harada et al. .................... 348/54
2011/0012511 A1* 1/2011 Watanabe ........................ 315/82

OTHER PUBLICATIONS

Brandes, et al.; "Aggregate Terminal Velocity/Temperature Relations"; Oct. 2008; American Meteorological Society; DOI: 10.1175/2008JAMC1869.1.

Kruger, et al.; "Two-Dimensional Video Disdrometer: A Description"; Journal of Atmospheric and Oceanic Technology; vol. 19; 2002 American Meteorological Society.

Muramoto, et al.; "Measurements of Falling Attitudes of Snowflakes Using Two Video Cameras"; Proc. NIPR Symp. Polar Meterol. Glaciol., e, 95-99, 1990.

* cited by examiner

SYSTEMS AND METHODS FOR IMAGING OF FALLING OBJECTS

RELATED APPLICATIONS

This application is a national stage entry of International Application No. PCT/US2010/059755, filed Dec. 9, 2010 which claims priority to U.S. Provisional Application No. 61/267,952, filed Dec. 9, 2009.

GOVERNMENT INTEREST

This invention was made with government support under Grant No. NNX06AE24G awarded by the National Aeronautics and Space Administration (NASA) and Grant No. ATM0649570 awarded by the National Science Foundation (NSF). The Government has certain rights to this invention.

BACKGROUND

Accurate characterization of the physical properties of atmospheric hydrometeors is useful for a broad range of practical and scientific applications. For example, hydrometeor diameter-mass-fallspeed relationships are useful components of weather and climate numerical models used in forecasting. Also, snowflake shape and size has an influence on snowpack density, and thus can be used for analyzing skiing conditions and avalanche susceptibility. The range of possible particle shapes and sizes is extremely broad, and includes raindrops, dendritic snowflakes, aggregated forms, graupel, and hail, and generally includes sizes ranging in diameters from less than a millimeter to several centimeters. Hydrometeor properties that have attracted past scientific interest include three-dimensional shape and size, fall-speed, and rotational motions about the particle center of mass.

A wide variety of electro-optical and communications devices and methods have been developed for inspecting and analyzing hydrometeors. Such systems have attempted to characterize hydrometeor structures and relate crystalline forms to changes in atmospheric electromagnetic attenuation, fall velocity, density, etc. Viewing of hydrometeors generally may take place in the field. However, such devices configured for viewing hydrometeors in the field have often involved significant manual intervention and have been unpredictable and/or unreliable. In addition, past devices have not provided sufficient visualization of the more minute features of hydrometeors, such as the crystalline structure of snowflakes or ice, in a continuous fashion or in an accurate manner. None of these instruments have provided three-dimensional visualization.

The ability to accurately and dependably study various particles in the field, including hydrometeors, can be useful in a variety of applications. For example, ski resorts may use detailed imagery of snowflakes to generate public interest and to assess snowpack conditions. Detailed information of hydrometeor size, shape, mass and fall-speed can be used to develop improved precipitation parameterizations for weather and climate forecast models. Measurements of snowflake size and morphology can be used to improve avalanche forecast models. Being able to document and image hydrometeors and properties of the hydrometeors, particularly at close range, is potentially useful for a wide variety of applications. For example, improvements in systems can be useful for documenting and imaging hydrometeors, as well as for providing information on the oscillation of hydrometeors, the conditions at which the hydrometeors tumble, the specific type of crystals that traverse a point along a line of sight, and the relationship between fall speed and particle size, color data, volume data, fall speed, and trajectory.

DETAILED DESCRIPTION

Reference will now be made to the exemplary embodiments illustrated, and specific language will be used herein to describe the same. It will nevertheless be understood that no limitation of the scope of the invention is thereby intended. Additional features and advantages of the invention will be apparent from the detailed description which follows, taken in conjunction with the accompanying drawings, which together illustrate, by way of example, features of the invention.

In describing and claiming the present invention, the following terminology will be used in accordance with the definitions set forth below.

As used herein, "electrically coupled" refers to a relationship between structures that allows electrical current to flow at least partially between them. This definition is intended to include aspects where the structures are in physical contact and those aspects where the structures are not in physical contact. Typically, two materials which are electrically coupled can have an electrical potential or actual current between the two materials. For example, two plates physically connected together by a resistor are in physical contact, and thus allow electrical current to flow between them. Conversely, two plates separated by a dielectric material are not in physical contact, but, when connected to an alternating current source, allow electrical current to flow between them by capacitive current. Moreover, depending on the insulative nature of the dielectric material, electrons may be allowed to bore through, or jump across the dielectric material when enough energy is applied.

As used herein, "optically coupled" refers to a relationship between structures that allows beams of light to flow at least partially between them. This definition is intended to include aspects where the structures are in physical contact and those aspects where the structures are not in physical contact.

As used herein, "adjacent" refers to near or close sufficient to achieve a desired affect. Although direct physical contact is most common and preferred in the structures or volumes of the present invention, adjacent can broadly allow for spaced apart features.

As used herein, the term "substantially" refers to the complete or nearly complete extent or degree of an action, characteristic, property, state, structure, item, or result. The exact allowable degree of deviation from absolute completeness may in some cases depend on the specific context. However, generally speaking the nearness of completion will be so as to have the same overall result as if absolute and total completion were obtained. The use of "substantially" is equally applicable when used in a negative connotation to refer to the complete or near complete lack of an action, characteristic, property, state, structure, item, or result. For example, a composition that is "substantially free of" particles would either completely lack particles, or so nearly completely lack particles that the effect would be the same as if it completely lacked particles. In other words, a composition that is "substantially free of" an ingredient or element may still actually contain such item as long as there is no measurable effect on the property of interest thereof.

As used herein, the term "about" is used to provide flexibility to a numerical range endpoint by providing that a given value may be "a little above" or "a little below" the endpoint with a degree of flexibility as would be generally recognized by those skilled in the art. Further, the term about explicitly includes the exact endpoint, unless specifically stated otherwise.

As used herein, a plurality of items, structural elements, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary.

Concentrations, amounts, and other numerical data may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges encompassed within that range as if each numerical value and sub-range is explicitly recited. As an illustration, a numerical range of "about 1 to about 5" should be interpreted to include not only the explicitly recited values of about 1 to about 5, but also include individual values and sub-ranges within the indicated range. Thus, included in this numerical range are individual values such as 2, 3, and 4 and sub-ranges such as from 1-3, from 2-4, and from 3-5, etc., as well as 1, 2, 3, 4, and 5, individually. This same principle applies to ranges reciting only one numerical value as a minimum or a maximum. Furthermore, such an interpretation can apply regardless of the breadth of the range or the characteristics being described.

By being able to document and image hydrometeors, information based upon the oscillation of hydrometeors, the conditions at which the hydrometeors tumble, the specific type of crystals that transverse a point along a line of sight, the relationship between fall speed and particle size, color data, volume data, fall speed, trajectory, etc. can be analyzed. Prior systems and methods utilized in imaging and obtaining data about falling objects have been limited in ability to accurately and adequately image and obtain such data about falling objects. Such systems have been costly, difficult to maintain, susceptible to weather elements, and have had issues with accuracy and reliability.

Described herein is an apparatus and method for accurately and reliably inspecting and imaging characteristics of falling particles, such as dust, sand, chips, flakes, hydrometeors, etc. The systems and methods can be used for imaging falling objects, such as particles, and for inspecting particles to determine physical characteristics, such as a crystalline structure of a snowflake. Though some of the examples in the following description are directed toward imaging of hydrometeors, such as snowflakes, these examples are for description purposes in explaining the technology and are not intended to be limiting. The systems and methods can be used for imaging falling objects of various types, sizes, shapes, and so forth. In a specific example, the falling objects may have a diameter in the range of less than a millimeter to many centimeters.

Figure 1:
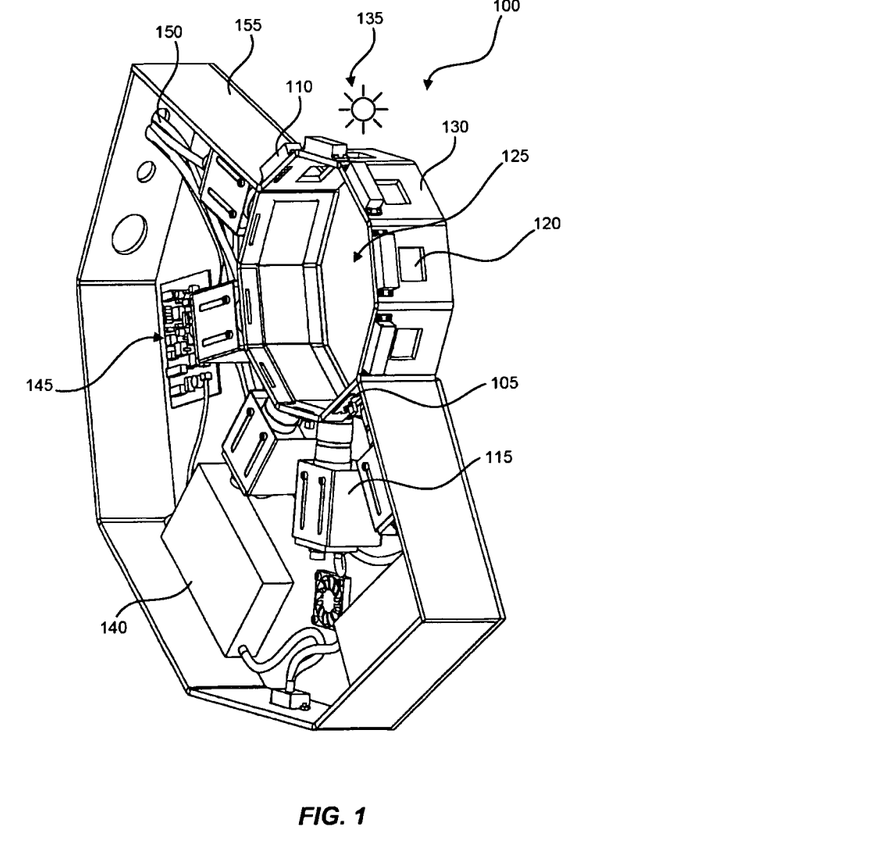
FIG. 1 is a perspective view of a system for imaging falling objects in accordance with an embodiment.

FIG. 1 illustrates a falling object image capture device 100 in accordance with an embodiment of the present technology. A plurality of motion sensors can be arranged at a first plurality of angles around a void 125. The motion sensors can have a common sensing point near the center of the void. The motion sensors can each include an emitter 105 and a detector 110. The detector can be positioned across the void from the emitter. For example, the detector and emitter can be attached on opposite sides of the void and be aligned such that a signal from the emitter is detected by the detector. The example illustrated in FIG. 1 includes five emitters and five detectors. However, the number of emitters and detectors can be varied according to a particular application. The emitter can be configured to emit electromagnetic energy (such as radio, microwave, or light rays) or optionally ultrasound in the direction of the detector. The detector can be configured to receive the emitted waves or rays. In one aspect, the waves or rays can be intermittent bursts of energy or light rather than a continual emission of energy or light.

The falling object image capture device 100 can include a plurality of cameras. The device can include any desired number of cameras. In the embodiment shown in the picture, the device includes 5 cameras 115. The plurality of cameras can be arranged at a second plurality of angles around the void. The plurality of cameras can be configured to capture images of a falling object within the void 125 from the second plurality of angles. The cameras can be configured to all capture images of the falling object substantially simultaneously. The camera angles can typically coincide with the motion sensor angles. However, other arrangements are also contemplated. In one aspect, the first and second pluralities of angles can be the same angles. For example, as shown in FIG. 1 the motion sensors can be arranged around the void at the same angles as the cameras and be positioned above the cameras.

The falling object image capture device 100 can include a frame having a plurality of walls 130 defining the void. In another example, a single wall, such as a circular or curved wall can define the void. In the example using multiple walls, the walls can form a polygonal cross-sectional shape. The polygonal shape typically can include an even number of walls such that for every wall with a camera and/or emitter, an opposite and/or parallel wall with a window 120 and/or detector can be provided. The window can allow light into the void to illuminate the falling object for imaging by the cameras. As will be described below, the system can include a light source positioned near the window, such as a strobe light or the like, for providing light through the window to illuminate the falling object substantially simultaneously with image capture.

The plurality of cameras can be configured to capture images of falling objects when the motion sensors detect motion within the void at the common sensing point. In one aspect, the cameras can be configured to capture images only when all of the motion sensors have detected motion. There is an area near the center of the void at which all of the motion sensors can sense motion at substantially the same time. Thus, the cameras may be configured to capture images when an object falls through that area near the center of the void. If an object falls to the side of the void and one or more of the image sensors are not triggered, then the system may be configured to not capture images of the falling object with the cameras. Capturing images when an object falls through the common sensing point can ensure that images of the falling object are captured by all of the cameras to be able to obtain a suitable image of the object from each of the plurality of angles.

In other configurations, the device can be configured to capture images when less than all of the motion sensors detect motion. Also, the device can be configured to capture images with fewer than all of the cameras in any given instance. In some cases, sufficient information can be gathered from fewer than all of the cameras for useful analysis. For example, fewer than all of the cameras may be used to capture images, or the cameras may be used to successively capture images of the falling object from different angles. Although FIG. 1 illustrates five cameras, additional or fewer cameras can be used. For example, cameras can be located all the way around the perimeter of the void (e.g. 8-10 cameras, which may correspond to an octagonal or decagonal wall configuration).

The device 100 can also include a light source. The light source can provide natural or artificial light. In one example, the light source comprises a flashing artificial light source. In a more specific example, the flashing light source can be a strobe light. The flashing light source can be configured to illuminate the falling object when images of the falling object are captured with the camera(s). The flashing light source can be configured to provide a flash of light in synchronization with image capture by the plurality of cameras. In other words, when the motion sensors have all detected motion at the common sensing point, the cameras and the flashing light source can be activated to capture images and provide light flashes substantially simultaneously. For example, the cameras and flashing light source can operate substantially immediately after motion is detected or may wait a predetermined time period after motion detection to begin operation. The cameras and the flashing light source can operate substantially simultaneously or successively. The system 100 can include a switch for switching between simultaneous and successive activation of the cameras/light sources. Providing a flash of light when the images are captured can enable capture of clearer images of the falling object. Images captured without the flash of light often may include at least a small amount of motion blur. In one aspect, the flash of light can have a very brief duration, such as a duration of a few milliseconds or microseconds. The flashing light can be configured to provide a single flash of light or to provide successive flashes of light at predetermined intervals.

A flashing light source can provide brief flashes of light which do not adversely affect falling objects, such as snowflakes. Continuous light sources can heat up the device, the void, and/or the falling object and may affect the falling object. For example, a crystalline structure of a snowflake may be altered or destroyed by heat from a continuous light source. A brief flash of light can have little or no impact on temperature and can be bright enough to provide good illumination of crystalline structure of snowflakes. In one aspect, the flash of light and activation of the cameras can provide a $1/100,000^{th}$ of a second exposure time. Because many falling objects have very small and intricate structures, the exposure time can be very short to get an acceptable resolution at the level of a few microns without image blurring.

The device 100 can be configured to determine fall speed of the falling object based on successive flashes of light. In another example, the system can include multiple sets of motion sensors at different heights around the void. The cameras can be activated to capture an image when the falling object passes a first set of motion sensors at a first height and can be subsequently activated again when the falling object passes a second set of motion sensors at a second height. The time delay between when the images are captured can be used to determine the fall speed of the object. In another example, the system can provide successive flashes of light to capture multiple images per frame while capturing images when the falling object is at different heights within the void. The multiple images per frame can be used to study the rotation of the falling object and to verify the velocity captured using the multiple sets of motion sensors.

The device can include a power source 140 or power supply for supplying electrical power to circuitry 145, the cameras 115, the emitters 105, the detectors 110, and so forth. The power source can include a battery for powering the device when an external power source is not available. In another example where an external power source is available, the power source can operate to convert an Alternating Current (AC) signal coming from the external power source into a usable Direct Current (DC) signal by stepping down the input voltage level with a transformer and then rectifying the signal to convert to DC. Once the DC signal is generated, the DC signal can be used to power all the various components of the system.

The device 100 can include an analysis engine. The analysis engine can be integrally formed within the frame of the device (e.g., circuitry 145) or may be on a separate device in communication with the falling object image capture device (e.g., via communication cables 150). The analysis engine can include circuitry and firmware or software for analyzing images. The analysis engine can be in communication with the plurality of cameras in order to provide analysis of images captured by the cameras. The analysis engine can be configured to analyze the captured falling object images and create an at least partial digital reconstruction of the falling object. For example, in the case of snowflakes, the analysis engine can be configured to detect a crystalline structure of the snowflakes and to create a digital reconstruction of the crystalline structure. Knowledge of the properties of the falling objects can enable a better understanding of the properties of an individual falling object and properties of a multitude of falling objects. For example, in the case of snowflakes, knowledge of the crystalline structure of the snowflakes can enable a better understanding of weather models, snowpack, and other forecasting models.

The device can include a housing 155. The housing can be configured to enclose the plurality of motion sensors, the plurality of cameras, and the flashing light source so as to at least partially prevent weather damage to components within the housing, and further configured to allow a falling object to enter the void. For example, the housing can be waterproof to prevent moisture from reaching the electronic components inside the housing. The void can be formed in the housing. Optionally, the housing can be small and compact so the device can be portable. For example, the size of the device may be approximately 18 inches in diameter or less. A height of the device may be approximately 4-5 inches. A diameter of the void can be approximately 6 inches. The above dimensions can also be varied to fit various applications and desired uses.

Figure 2A:
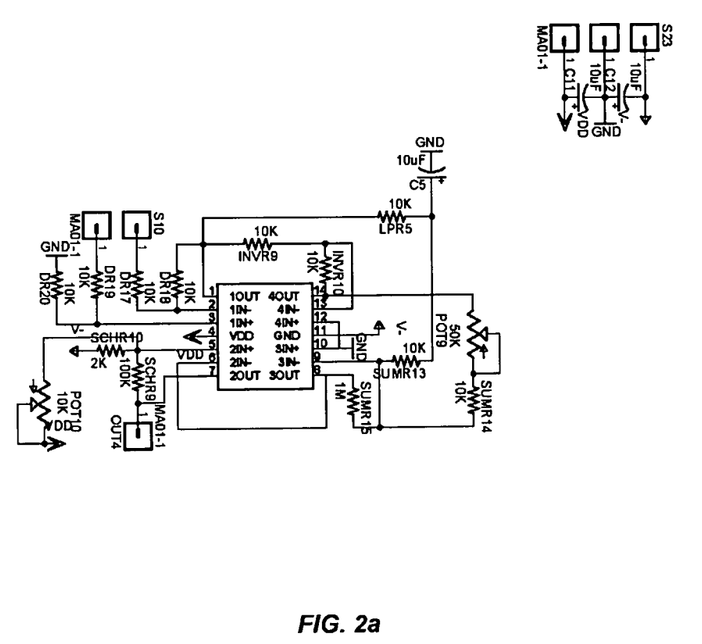
FIGS. 2a-2c are schematics of float removal Schmitt triggers for use in accounting for drifting baselines in accordance with an embodiment.
Figure 2B:
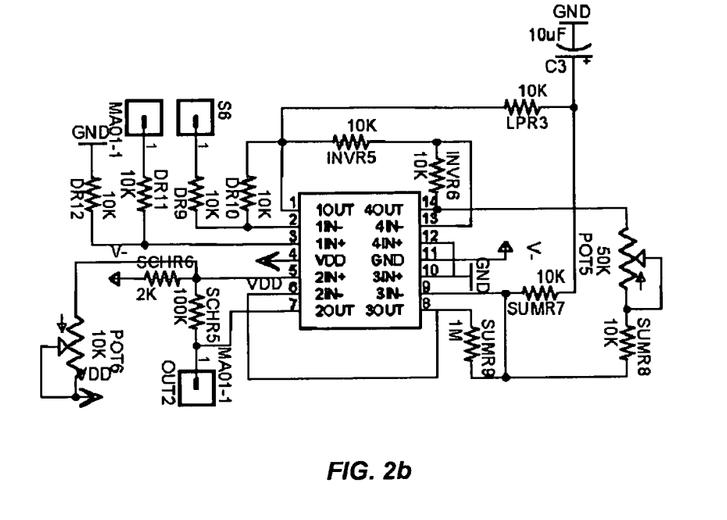
Figure 2C:
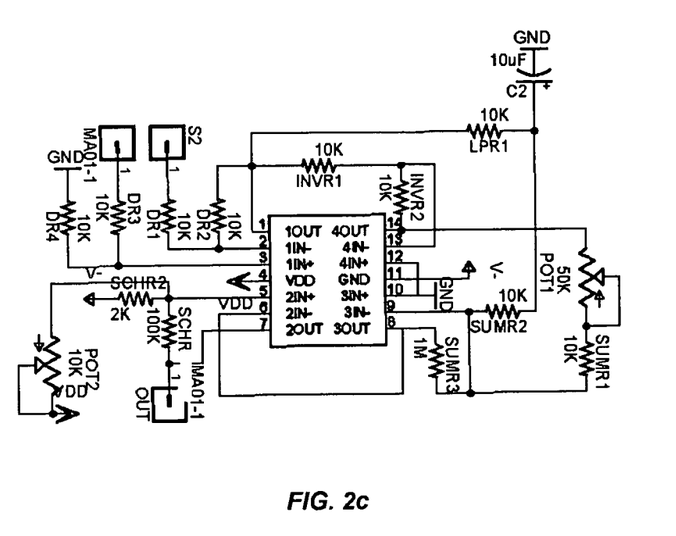

In one aspect, the device 100 can include circuitry 145 to provide a voltage offset to provide a zero baseline voltage for comparison in detecting motion using the plurality of motion sensors. FIGS. 2a-2c are schematic diagrams of float removal Schmitt triggers for use in accounting for drifting baselines for five motion detectors similarly as shown in FIG. 1. FIG. 2a illustrates a circuit for a single camera and power entry portion of the Schmitt trigger. FIGS. 2b-2c illustrate four similar circuits, resulting in five circuits for five cameras. Lighting conditions can change in a non-controlled environment, such as the outdoors where snowflakes fall. Therefore, accounting for drifting baselines in the circuit can enable the system to accurately detect falling objects even when the lighting changes. Essentially the circuits take a signal and feed the signal back into itself and compare the original and the feedback signal. Where lighting does not change, the signal will be substantially the same. If a low-pass filter is added to one of the signals, as in the figures, when a snowflake or other object falls through the void a higher frequency signal will be blocked but lower frequency signals, which are slower, can separately be used to accommodate for lighting, temperature, and other changes in the environment. In other words, because a quick pulse is blocked from one of the signals, the signals are different when compared so the cameras can be triggered.

In another embodiment, the device 100 of FIG. 1 includes a system configured to manage operation of the device. A motion sensor controller, which can be included in circuitry 145, can be used to control a plurality of motion sensors and to generate a camera activation signal when all of the plurality of motion sensors sense motion at a substantially similar time. The system can include a camera activation module, which may also be included in circuitry 145. The camera activation module can be in communication with the motion sensor controller. The camera activation module can receive the camera activation signal and activate the cameras to capture a plurality of images of the falling object from multiple different angles. A light source activation module, which may also be included in circuitry 145, can be in communication with the motion sensor controller and the camera activation module. The light source activation module can receive the camera activation signal. In response to receiving the camera activation signal the light source activation module can activate a flashing light source to provide a flash of light in synchronization with image capture by the cameras to illuminate the falling object when images of the falling object are captured.

The system can also include an edge detection module. The edge detection module can be used to detect edges of the falling object. Various edge detection techniques are known in the art. Examples of edge detection techniques usable by the edge detection module include Gaussian and Laplace edge detection, among others. The system can include a classification module. The classification module can create a falling object classification based on a shape of the detected edges for falling objects having edges which do not match a known classification. The classification module can be in communication with the edge detection module to determine the shape of the edges. The classification module can also be in communication with a database for storing classifications. The classification module can compare the detected edges with known classifications from the database to determine whether the detected edges match a known classification. When the detected edges do not match a known classification, the classification module can create a new classification. When the detected edges do match a known classification, the classification module can classify the falling object according to the detected edges.

The system can include a digital reconstruction module. The digital reconstruction module can be used to create a digital three dimensional model of the falling object. The digital reconstruction module can be in communication with the edge detection module to receive information about the edges of the falling object. For example, in the case of snowflakes the edges may comprise the crystalline structure throughout the snowflake. Because the cameras are positioned at multiple angles around the snowflake, structure of the snowflake around at least a part of a circumference of the snowflake can be determined from the captured images. The structure can be used to create a partial or complete digital reconstruction of the snowflake in two dimensions or three.

In a simplified example, the edge detection module can detect outermost edges of the falling object to create a shadow. The digital reconstruction module can intersect the shadows to create a volume estimation for the falling object. A disdrometer can be used in combination with the reconstruction module to verify the mass of the falling object. The disdrometer can be operatively connected to the device so as to allow measurement across the void of falling objects.

The system can include an analysis module. The analysis module can be used to analyze the images captured by the cameras to identify one or more properties of the falling object. For example, the analysis module can determine properties such as dimension, color, object type, three-dimensional shape, volume data, fall speed, and trajectory, among others.

Each of the above modules can be provided as software which analyzes the corresponding data. The modules can be hard-coded into the device or stored in memory and accessed via a computer processing device (e.g. CPU). The data processing can be done via on-device processing. Alternately, raw data can be stored in the device for later retrieval and downloading to a computing device having the corresponding modules installed thereon. For example, stored data can be retrieved via a data connection (e.g. USB, firewire, wireless, etc.) to a computer having the analysis engine and corresponding modules installed thereon as a software package.

The various modules described above can be in the form of hardware, firmware, software, and/or combinations thereof. The modules can be formed in the circuitry 145 or can use the circuitry to perform various operations, or can be located externally from the housing 155, such as in an electronically connected computing system. The modules can be in communication with a processor for performing various operations. In one example, one or more of the modules comprises computer readable code, stored on a non-transitory computer readable storage medium, which when executed by the processor causes a system to perform the described operations.

Figure 3:
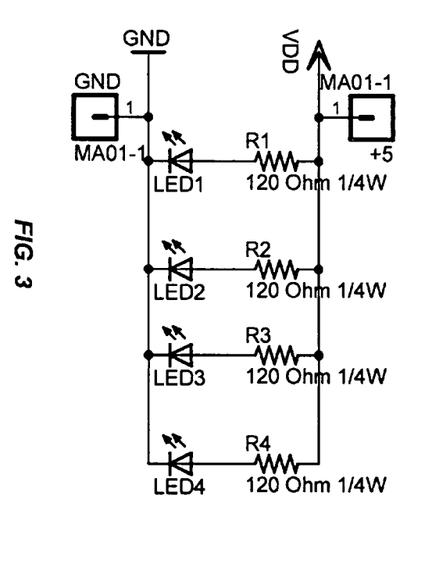
FIG. 3 is a schematic of a circuit for an infrared detector for use in a falling object imaging system in accordance with an embodiment.
Figure 4:
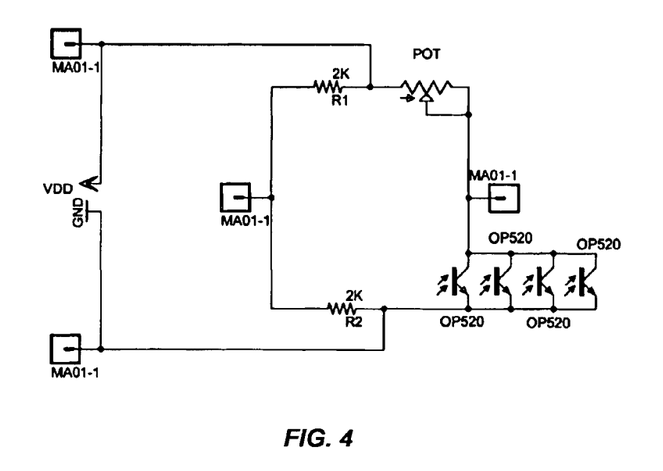
FIG. 4 is a schematic of a circuit for an infrared emitter for use in a falling object imaging system in accordance with an embodiment.

FIGS. 3 and 4 are schematics of circuits for infrared emitters and detectors for use in a falling object imaging system in accordance with an embodiment. The emitters shown in FIG. 3 include light emitting diodes and circuitry for causing the light emitting diodes to emit light. The detector circuit of FIG. 4 illustrates a Wheatstone bridge which balances at least two signals against one another so as to zero voltage across the bridge. The signals subtracted or compared are the signal emitted by the emitter and the signal detected by the detector. When the signals are the same and subtraction of one signal from the other results in substantially zero difference, a falling object has not been detected. When a falling object obstructs the path of the emitted signal, the detected signal will change. The circuit includes an amplifier to amplify the change in the signal because the change may be very small. When the changed signal is compared with the emitted signal, the difference will not be zero and the cameras can be triggered (e.g. via a Schmitt trigger circuit) to capture images of the object.

Figure 5:
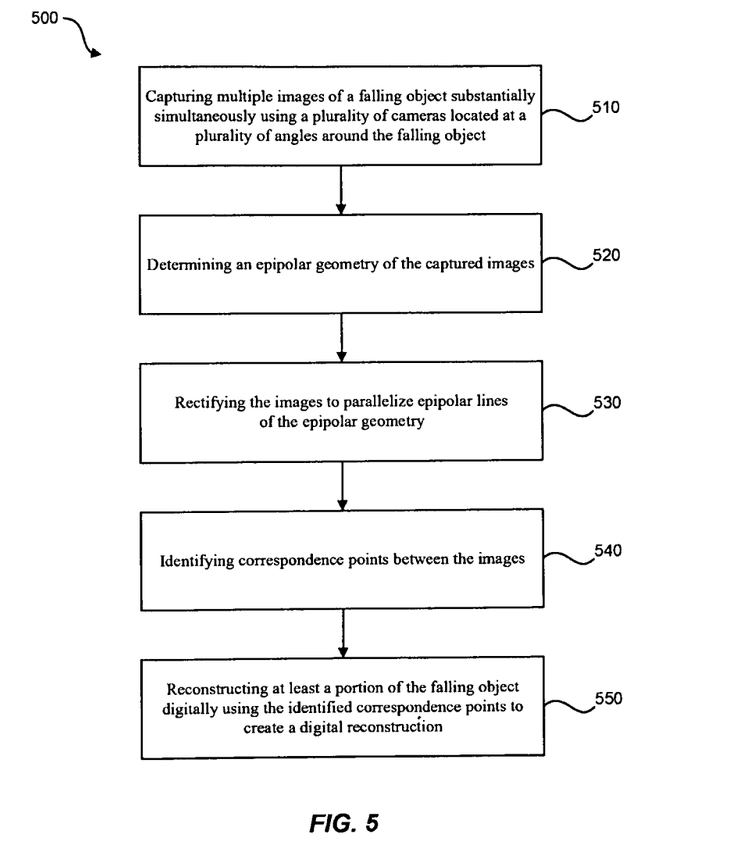
FIG. 5 is a flow diagram of a method for imaging falling objects in accordance with an embodiment.

FIG. 5 illustrates a method for imaging falling objects in accordance with an embodiment. Multiple images of a falling object can be captured substantially simultaneously using a plurality of cameras located at a plurality of angles around the falling object. An epipolar geometry of the captured images can be determined. For example, a processor can be used to process data from the images to determine the epipolar geometry. The images can be rectified to parallelize epipolar lines of the epipolar geometry. Correspondence points between the images can be identified. The correspondence points from the different images can be used in reconstructing at least a portion of the falling object digitally.

The method can further include calculating at least one property of the falling object using the digital reconstruction of the at least a portion of the falling object. Examples of properties which can be calculated include dimension, color, object type, three-dimensional shape, volume data, fall speed, and trajectory, among others. The method can include calibrating exposure properties for the cameras according to environmental conditions to capture images of the falling object. The step of capturing images from the method can further include motion sensing from a plurality of angles to determine presence of the falling object located at a predetermined location in order to coordinate a trigger time common to each of the plurality of cameras. The trigger time can also trigger a flash light source to illuminate the falling object.

In one aspect, the falling object can be a hydrometeor such as a snowflake, raindrop, piece of hail, etc. or may be a non-hydrous particle such as a dust particle, a pebble, a woodchip, etc. The method can include detecting edges of the falling object in the digital reconstruction using an edge detection module. A classification can then be created based on a shape of the detected edges. Alternatively, if a classification already exists for the detected edges, the falling object can be classified by comparing the detected edges with classifications stored in a database.

The method can also include automated zooming of the cameras. For example, the automated zooming can be performed by object segmentation and analyzing the segmented object in a captured image to determine a percentage of the image occupied by the object, including the segmented object and zooming and focusing at least one of cameras to fit the segmented object to a predetermined percentage of the image based on an average best fit for a known segmented object.

Figure 6:
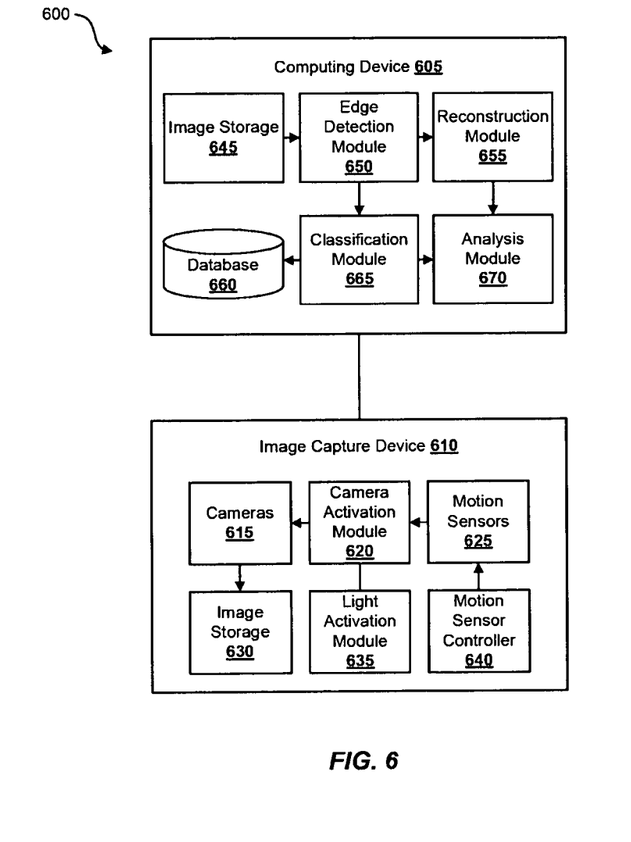
FIG. 6 is a block diagram of a system for imaging falling objects in accordance with an embodiment.

FIG. 6 illustrates a system 600 for imaging falling objects in accordance with an embodiment of the technology. The system includes a computing device 605 and an image capture device 610. The image capture device includes a motion sensor controller 640, motion sensors 625, as well as camera and light activation modules 620, 635. Cameras 615 can be used to capture images of falling objects and can store the captured images on an image storage device 630. The operation of the various components of the image capture device has been described in further detail above.

The computing device 605 in this example is separate from the image capture device 610. The allocation of components between the computing device and the image capture device can vary with different applications and designs. The computing device can include a personal computer, a networked server, or any other of a variety of different types of computing devices. The computing device can further comprise a plurality of computing devices. For example, the image capture device can be in electronic communication with a server (i.e., a computing device) and can transmit captured images from the image capture device image storage 630 to an image storage device in communication with the server. A user can access the images from the server via a workstation computing device to process the images with the various modules shown as components of the computing device. Other configurations of systems are also contemplated and are considered within the scope of this disclosure.

For simplicity, the computing device 605 in FIG. 6 is illustrated as a single computing device. However, one or more of these modules can be provided by multiple computing devices which are parallelized or otherwise cooperatively communicate. The computing device can receive captured or stored images from the image capture device 610. The computing device can optionally store the received images on an image storage device 645, such as a hard drive, optical disc, flash memory, and the like. The computing device includes an edge detection module 650 for detecting edges of the falling object captured in the images. A classification module 665 can be in communication with an object database 660 for identifying an object type based on the detected images. The object database can include a plurality of object types defined by object structure, such as edges. An image reconstruction module 655 can reconstruct a digital model of the imaged object for analysis by an analysis module 670. The analysis module can also receive input from the classification module 665 to use in performing the analysis. The operations of the various modules and components of the computing device have been described in further detail above.

The methods and systems of certain embodiments may be implemented in hardware, software, firmware, or combinations thereof. In one embodiment, the method can be executed by software or firmware that is stored in a memory and that is executed by a suitable instruction execution system. If implemented in hardware, as in an alternative embodiment, the method can be implemented with any suitable technology that is well known in the art.

The various engines, tools, or modules discussed herein may be, for example, software, firmware, commands, data files, programs, code, instructions, or the like, and may also include suitable mechanisms.

Reference throughout this specification to "one embodiment", "an embodiment", or "a specific embodiment" means that a particular feature, structure, or characteristic described in connection with the embodiment is included in at least one embodiment of the present invention. Thus, the appearances of the phrases "in one embodiment", "in an embodiment", or "in a specific embodiment" in various places throughout this specification are not necessarily all referring to the same embodiment. Furthermore, the particular features, structures, or characteristics may be combined in any suitable manner in one or more embodiments.

Other variations and modifications of the above-described embodiments and methods are possible in light of the foregoing disclosure. Further, at least some of the components of an embodiment of the invention may be implemented by using a programmed general purpose digital computer, by using application specific integrated circuits, programmable logic devices, or field programmable gate arrays, or by using a network of interconnected components and circuits. Connections may be wired, wireless, and the like.

It will also be appreciated that one or more of the elements depicted in the drawings/figures can also be implemented in a more separated or integrated manner, or even removed or rendered as inoperable in certain cases, as is useful in accordance with a particular application.

Also within the scope of an embodiment is the implementation of a program or code that can be stored in a machine-readable medium to permit a computer to perform any of the methods described above.

Additionally, the signal arrows in the Figures are considered as exemplary and are not limiting, unless otherwise specifically noted. Furthermore, the term "or" as used in this disclosure is generally intended to mean "and/or" unless otherwise indicated. Combinations of components or steps will also be considered as being noted, where terminology is foreseen as rendering the ability to separate or combine is unclear.

As used in the description herein and throughout the claims that follow, "a", "an", and "the" includes plural references unless the context clearly dictates otherwise. Also, as used in the description herein and throughout the claims that follow, the meaning of "in" includes "in" and "on" unless the context clearly dictates otherwise.

Various functions, names, or other parameters shown in the drawings and discussed in the text have been given particular names for purposes of identification. However, the functions, names, or other parameters are only provided as some possible examples to identify the functions, variables, or other parameters. Other function names, parameter names, etc. may be used to identify the functions, or parameters shown in the drawings and discussed in the text.

While the forgoing examples are illustrative of the principles of the present invention in one or more particular applications, it will be apparent to those of ordinary skill in the art that numerous modifications in form, usage and details of implementation can be made without the exercise of inventive faculty, and without departing from the principles and concepts of the invention. Accordingly, it is not intended that the invention be limited, except as by the claims set forth below.

What is claimed is:

1. A method of imaging falling objects, comprising:
capturing multiple images of a falling object substantially simultaneously using a plurality of cameras located at a plurality of angles around the falling object;
determining an epipolar geometry of the captured images;
rectifying the images to parallelize epipolar lines of the epipolar geometry;
identifying correspondence points between the images; and
reconstructing at least a portion of the falling object digitally using the identified correspondence points to create a digital reconstruction.

2. A method as in claim 1, further comprising calculating at least one property of the falling object using the digital reconstruction of the at least a portion of the falling object.

3. A method as in claim 2, wherein the at least one property of the falling object is selected from the group consisting of dimension, color, object type, three-dimensional shape, volume data, fall speed, and trajectory.

4. A method as in claim 1, further comprising calibrating exposure properties for the plurality of cameras according to environmental conditions to capture images of the falling object.

5. A method as in claim 1, wherein the step of capturing further includes motion sensing from a plurality of angles to determine presence of the falling object located at a predetermined location in order to coordinate a trigger time common to each of the plurality of cameras.

6. The method of claim 5, wherein the trigger time further triggers a flash light source to illuminate the falling object.

7. A method as in claim 1, wherein the falling object is a hydrometeor selected from the group consisting of snowflake, raindrop, hail, dust, and combinations thereof.

8. A method as in claim 7, wherein the falling object is a hydrometeor and the method further comprises:
detecting edges of the hydrometeor in the digital reconstruction using an edge detection module; and
creating a hydrometeor classification based on a shape of the detected edges.

9. A method as in claim 7, wherein the falling object is a hydrometeor and the method further comprises:
detecting edges of the hydrometeor in the digital reconstruction using an edge detection module; and
classifying the hydrometeor by comparing the detected edges with hydrometeor classifications stored in a database.

10. A method as in claim 1, further comprising automated zooming of the plurality of cameras by:
analyzing a segmented object in a captured image to determine a percentage of the image including a segmented object; and
zooming and focusing at least one of the plurality of cameras to fit the segmented object to a predetermined percentage of the image based on an average best fit for a known segmented object.

11. A falling object image capture device, comprising:
a plurality of motion sensors arranged at a first plurality of angles around a void and having a common sensing point;
a plurality of cameras arranged at a second plurality of angles around the void and configured to capture images of a falling object within the void when the plurality of motion sensors detect motion within the void at the common sensing point; and
a flashing light source configured to provide a flash of light in synchronization with image capture by the plurality of cameras to illuminate the falling object when images of the falling object are captured.

12. A device as in claim 11, further comprising an analysis engine configured to analyze the captured falling object images and create an at least partial digital reconstruction of the falling object.

13. A device as in claim 11, wherein the camera is configured to capture the images of the falling object only when all of the plurality of motion sensors have detected motion within the void at the common sensing point.

14. A device as in claim 11, further comprising a housing configured to enclose the plurality of motion sensors, the plurality of cameras, and the flashing light source so as to at least partially prevent weathering and damage to components within the housing, and further configured to allow a falling object to enter the void.

15. A device as in claim 11, further comprising circuitry to provide a voltage offset to provide a zero baseline voltage for comparison in detecting motion using the plurality of motion sensors.

16. A system for operating a falling object image capture device, comprising:
a motion sensor controller configured to control a plurality of motion sensors and to generate a camera activation signal when all of the plurality of motion sensors sense motion at a substantially similar time;
a camera activation module in communication with the motion sensor controller, wherein the camera activation module is configured to receive the camera activation signal and activate a plurality of cameras to capture a plurality of images of the falling object from a plurality of angles;
a light source activation module in communication with the motion sensor controller and the camera activation module, wherein the light source activation module is configured to receive the camera activation signal and in response activate a flashing light source to provide a flash of light in synchronization with image capture by the plurality of cameras to illuminate the falling object when images of the falling object are captured.

17. A system as in claim 16, further comprising an edge detection module configured to detect edges of the falling object.

18. A system as in claim 17, further comprising a classification module configured to:
   create a falling object classification based on a shape of the detected edges for falling objects having edges which do not match a known classification; and
   classify the falling object when the detected edges match a known classification by comparing the detected edges with falling object classifications stored in a database.

19. A system as in claim 16, further comprising a digital reconstruction module configured to create a digital three dimensional model of the falling object.

20. A system as in claim 16, further comprising an analysis module configured to analyze the images captured by the plurality of cameras to identify one or more properties of the falling object selected from the group consisting of: dimension, color, object type, three-dimensional shape, volume data, fall speed, and trajectory.

* * * * *